United States Patent
Hanaoka

(10) Patent No.: US 6,551,492 B2
(45) Date of Patent: Apr. 22, 2003

(54) ELECTROLYZED WATER OF ANODE SIDE AND PROCESS FOR PRODUCTION THEREOF

(75) Inventor: Kokichi Hanaoka, 1187-4, Oaza-Ueda, Ueda-shi, Nagano 386-0001 (JP)

(73) Assignees: Mikuni Corporation, Tokyo (JP); Kokichi Hanaoka, Nagano (JP)

(*) Notice: Subject to any disclaimer, the term of this patent is extended or adjusted under 35 U.S.C. 154(b) by 0 days.

(21) Appl. No.: 09/867,221

(22) Filed: May 29, 2001

(65) Prior Publication Data

US 2002/0027079 A1 Mar. 7, 2002

(30) Foreign Application Priority Data

Jun. 8, 2000 (JP) ........................................ 2000-172538

(51) Int. Cl.[7] ............................................... C02F 1/461
(52) U.S. Cl. ........................................ 205/742; 205/746
(58) Field of Search .................................. 205/742, 746

(56) References Cited

U.S. PATENT DOCUMENTS 5,736,027 A * 4/1998 Nakamura ................ 205/742

FOREIGN PATENT DOCUMENTS

| EP | 0987222 | 3/2000 |
|---|---|---|
| JP | 8229563 | 2/1995 |
| JP | 1133552 | 2/1999 |
| JP | 09276535 | 4/1999 |

* cited by examiner

Primary Examiner—Arun S. Phasge
(74) Attorney, Agent, or Firm—Norris McLaughlin & Marcus, P.A.

(57) ABSTRACT

According to the present invention, there is disclosed:

an electrolyzed water of anode side containing less than 0.1 mM of a water-soluble inorganic salt, 1 to 50 mM of ascorbic acid and 8 to 15 mg/l of dissolved oxygen and having a dismutation activity for superoxide radicals; and a process for producing an electrolyzed water of anode side having a dismutation activity for superoxide radicals, which comprises electrolyzing an aqueous electrolytic solution containing less than 0.1 mM of a water-soluble inorganic salt and 1 to 50 mM of ascorbic acid and then taking out the electrolyzed water of anode side generated.

5 Claims, 11 Drawing Sheets

ELECTROLYZED WATER OF ANODE SIDE AND PROCESS FOR PRODUCTION THEREOF

BACKGROUND OF THE INVENTION

1. Field of the Invention

The present invention relates to an electrolyzed water of anode side having a dismutation activity for superoxide radicals, as well as to a process for producing such an electrolyzed water. More particularly, the present invention relates to a process for producing an electrolyzed water of anode side by electrolyzing an aqueous electrolytic solution containing only ascorbic acid as an electrolytic aid and taking out the electrolyzed water generated at the anode side, as well as to an electrolyzed water of anode side produced by such a process, having a dismutation activity for superoxide radicals.

2. Description of the Related Art

A technique is well known in which a dilute aqueous solution of an electrolyte such as alkali metal chloride or the like is electrolyzed in an electrolytic cell comprising inactive electrodes made of platinum, a platinum alloy or the like and a separating membrane placed between the electrodes and the electrolyzed water of low pH (acidic water) generated at the anode side is taken out to utilize it for sterilization or disinfection. As the separating membrane, there is used a charged membrane (an ion exchange resin film) or a non-charged membrane of porous structure.

The electrolyzed water of anode side contains hypochlorous acid therein. In utilization of the electrolyzed water of anode side for sterilization or disinfection, the strong oxidizing action and chlorinating action of hypochlorous acid is utilized. Such utilization of the electrolyzed water of anode side is widely conducted in medical institutions, etc. Further, the ozone and dissolved oxygen present in a small amount in the electrolyzed water of anode side promotes granulation; therefore, the electrolyzed water of anode side is being studied as an aid in surgical treatment.

Meanwhile, the electrolyzed water of cathode side (alkaline water) generated at the cathode side can be obtained also by electrolyzing a tap water in place of the above-mentioned dilute aqueous solution of an electrolyte. The electrolyzed water of cathode side has been utilized for drinking, etc. In U.S. Pat. No. 5,736,027, there is disclosed other technique for producing an electrolyzed water, which comprises electrolyzing the above-mentioned aqueous electrolytic solution or a tap water by adding an organic acid (e.g. ascorbic acid or gallic acid) as an additive and not as an electrolytic aid.

In this technique, ascorbic acid is used in the presence of an electrolytic aid. The purpose of adding ascorbic acid is to (a) control the pH of electrolyzed water of cathode side and (b) remove the free chlorine in electrolyzed water of anode side.

Incidentally, the well-known Kolbe reaction (this has no direct connection with the above technique) is a reaction in which an organic acid (e.g. a carboxylic acid) is electrolyzed to release carbon dioxide and also generate a compound wherein two organic acid residues are combined, at the anode side. For example, there has long been known a technique in which citric acid is generated from acetic acid according to the Kolbe reaction.

Ascorbic acid has OH group at the 2-position and 3-position of the molecule. In an acidic state, the —OH of the 3-position is dissociated into —$O^-$ and $H^+$, showing an acidity. In an alkaline state, the —OH of the 2-position is dissociated into —$O^-$ and $H^+$. However, the degree of this dissociation is low and, therefore, ascorbic acid has never been used as an electrolytic aid. Incidentally, the electrolysis mechanism of aqueous ascorbic acid solution is complicated and the intermediates generated in electrolysis have not been specified; however, the mechanism is recognized to be basically a redox reaction.

Ascorbic acid is a strong reducing agent by itself. It is well known that ascorbic acid undergoes autoxidation in an aqueous solution and comes to have a lower reducing power. Ascorbic acid undergoes autoxidation generally according to the following reaction scheme (1).

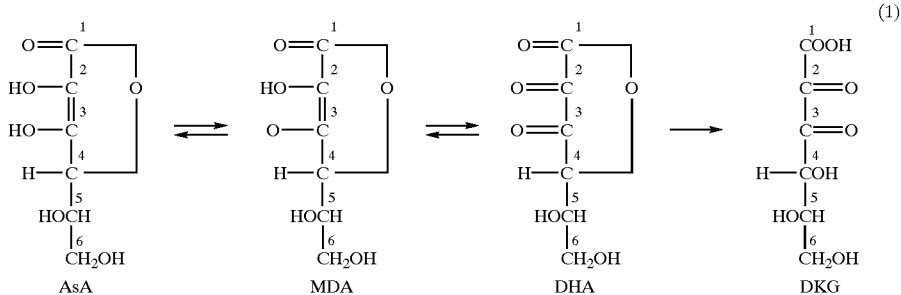

In the above, AsA, MDA, DHA and DKG refer to ascorbic acid, monodehydroascorbic acid, dehydroascorbic acid and 2,3-diketogulonic acid, respectively.

In recent years, it has been made clear that ascorbic acid allows superoxide radicals (this is well-known as a reactive oxygen) to dismutate and disappear. Therefore, ascorbic acid has come to draw attention as an antioxidant.

The dismutation reaction of superoxide radicals are expressed by the following formula (2).

$$O^-_2 \cdot + O^-_2 \cdot + 2H^+ \rightarrow H_2O_2 + O_2 \tag{2}$$

That is, superoxide radicals disappear and hydrogen peroxide is generated.

As described above, ascorbic acid has an action of allowing superoxide to disappear. However, there has hitherto been no report regarding an electrolyzed water of anode side having a dismutation activity for superoxide radicals, obtained by electrolysis of an aqueous ascorbic acid solution.

SUMMARY OF THE INVENTION

The present inventor paid attention to the ascorbic acid's dismutation activity for superoxide radicals and made a study to obtain an electrolyzed water of anode side having the above action. As a result, the present inventor found out that an electrolyzed water of anode side having a dismutation activity for superoxide radicals can be obtained by electrolyzing an aqueous solution containing only ascorbic acid in a relatively low concentration without using any inorganic electrolyte (e.g. a water-soluble metal salt) as an electrolytic aid.

The present invention has been completed based on the above finding and aims at providing an electrolyzed water of anode side having a dismutation activity for superoxide radicals.

The present invention lies in the following [1] to [5].

[1] An electrolyzed water of anode side containing less than 0.1 mM of a water-soluble inorganic salt, 1 to 50 mM of ascorbic acid and 8 to 15 mg/l of dissolved oxygen and having a dismutation activity for superoxide radicals.

[2] A process for producing an electrolyzed water of anode side having a dismutation activity for superoxide radicals, which comprises electrolyzing an aqueous electrolytic solution containing less than 0.1 mM of a water-soluble inorganic salt and 1 to 50 mM of ascorbic acid and then taking out the electrolyzed water of anode side generated.

[3] A process for producing an electrolyzed water of anode side having a dismutation activity for superoxide radicals, according to the above [2], wherein the electrolysis is conducted using an electrolytic cell having a separating membrane.

[4] A process for producing an electrolyzed water of anode side having a dismutation activity for superoxide radicals, according to the above [2], wherein the electrolysis is conducted at a current density of 0.003 to 0.03 A/cm$^2$.

[5] A process for producing an electrolyzed water of anode side having a dismutation activity for superoxide radicals, according to the above [2], wherein an aqueous electrolytic solution containing less than 0.1 mM of a water-soluble inorganic salt and 1 to 50 mM of ascorbic acid is fed into a continuous flowing type electrolytic cell having a separating membrane, at a flow rate of 500 to 3,000 ml/min and is electrolyzed continuously at a current density of 0.003 to 0.03 A/cm$^2$.

When an aqueous electrolytic solution is electrolyzed in order to utilize the obtained electrolyzed water for drinking, sterilization and disinfection, there is used, as the aqueous electrolytic solution, a tap water or an aqueous solution obtained by adding to, a tap water, a water-soluble inorganic salt such as sodium chloride, potassium chloride or the like. In the case of a tap water, a certain amount of inorganic salts are present therein and they act as an electrolyte.

Meanwhile, there are reports (e.g. Japanese Patent Application laid open 11-33552) on a technique of electrolyzing an electrolyte- and ascorbic acid-added aqueous solution to produce an electrolyzed water. In this technique, ascorbic acid is used as an additive for removal of alkalinity. There is also known a technique (Japanese Patent Application laid open 8-229563) of electrolyzing an aqueous electrolytic solution containing ascorbic acid as an additive and reducing the hypochlorous acid present in the electrolyzed water of anode side generated, with ascorbic acid to suppress the generation of free chlorine in the electrolyzed water.

In all of these techniques, the aqueous electrolytic solution used contains an electrolyte (consisting of a water-soluble inorganic salt) as an electrolytic aid and, in addition, ascorbic acid. This ascorbic acid is used as an additive not directly associated with electrolysis.

When an aqueous electrolytic solution containing an electrolyte (e.g. sodium chloride) as an electrolytic aid and ascorbic acid as an additive is electrolyzed, the following reactions take place generally.

1. Cathode side

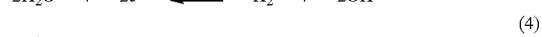
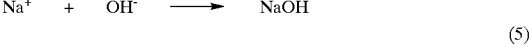
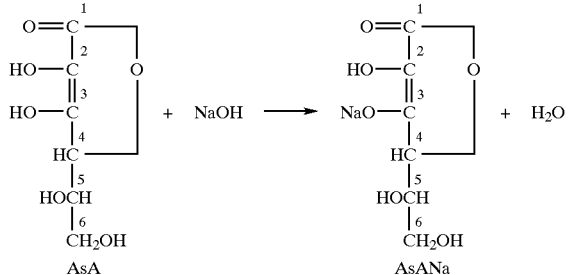

In the above, AsANa refers to sodium ascorbate. In the electrolyzed water of cathode side, the H$^+$ of the 3-position of ascorbic acid is substituted with sodium ion, whereby ascorbic acid becomes a sodium salt. As a result, only the H$^+$ of the 2-position can have a dismutation activity for superoxide radicals. Thus, the dismutation activity of ascorbic acid is reduced to half.

2. Anode side

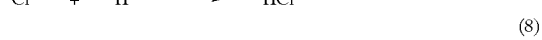
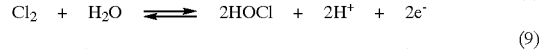
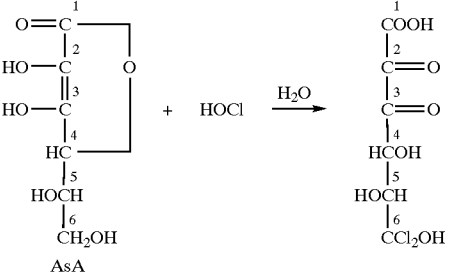

In the anode side, as shown in the above formula (9), both the H$^+$ of the 2-posiiton and the H$^+$ of the 3-posiiton, of ascorbic acid disappear owing to the chlorinating and oxidizing actions of hypochlorous acid; as a result, there is obtained no dismutation activity for superoxide radicals.

The above is electrolytic reactions occurring at two electrodes when an aqueous electrolytic solution containing an electrolyte as an electrolytic aid and ascorbic acid as an additive is electrolyzed. In this case, a dismutation activity for superoxide radicals is obtained only at the cathode side; however, the dismutation activity is reduced by the formation of sodium ascorbate.

In the anode side, as mentioned previously, both the H$^+$ of the 2-position and the H$^+$ of the 3-position, of ascorbic acid disappear owing to the chlorinating and oxidizing actions of hypochlorous acid; as a result, there is obtained no dismutation activity for superoxide radicals.

Meanwhile, when an aqueous electrolytic solution containing only ascorbic acid as an electrolyte is electrolyzed, the following reactions take place at two electrodes.

1. Cathode side $$2H_2O + 2e^- \rightleftharpoons H_2 + 2OH^- \quad (10)$$

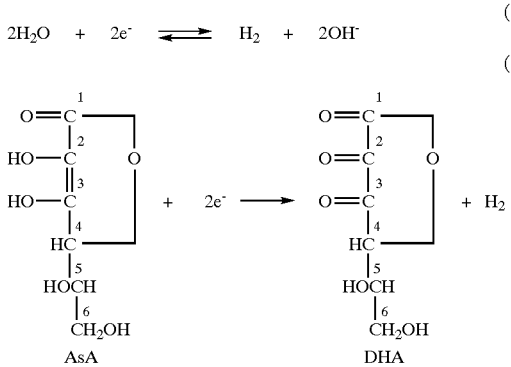

(11)

As shown in the formula (11), electrolysis allows the 2-position and 3-position hydrogen atoms of ascorbic acid to give rise to an electrophilic reaction on the cathode, whereby hydrogen gas is generated at the cathode side. Since the DHA generated by electrolysis is unable to release $H^+$, the electrolyzed water of cathode side has no dismutation activity for superoxide radicals. Further, since ascorbic acid anion is transferred to the anode side, there is no dismutation activity for superoxide radicals by ascorbic acid anion, either.

2. Anode side $$2H_2O \rightleftharpoons O_2 + 4H^+ + 4e^- \quad (12)$$

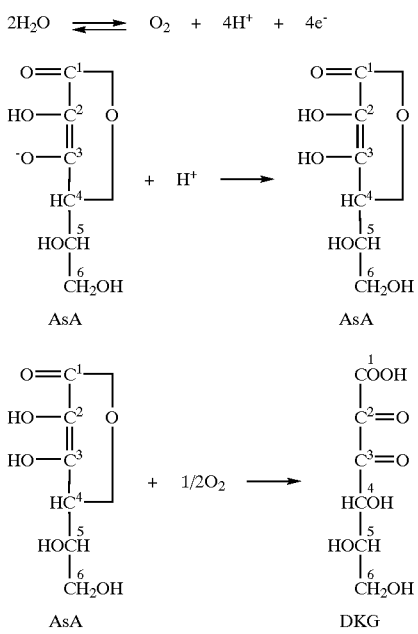

(13)

(14)

As shown in the formula (13), ascorbic acid anion reacts with the $H^+$ generated by anode oxidation of water and becomes ascorbic acid. Meanwhile, as shown in the formula (14), the oxygen gas generated by anode oxidation of water is consumed by oxidizing ascorbic acid into 2,3-diketogulonic acid (DKG) and, as a result, the dissolved oxygen amount in electrolyzed water of anode side is decreased; however, this proportion is not large.

Further at the anode, in addition to the reaction shown in the formula (13), $H^+$ is present in slight excess owing to the difference in diffusion rate between ascorbic acid anion and $H^+$; therefore, the amount of $H^+$ is more than when only ascorbic acid is present. As a result, the dismutation ability for superoxide radicals is high at the anode side.

The above can be summarized as follows.

(1) When an aqueous electrolytic solution is electrolyzed which contains a water-soluble electrolyte (e.g. sodium chloride or potassium chloride) as an electrolytic aid and ascorbic acid as an additive, the electrolyzed water of cathode side has a dismutation activity but the action is low because ascorbic acid is consumed in the form of sodium or potassium ascorbate. The electrolyzed water of anode side contains hypochlorous acid, and this hypochlorous acid consumes the most part of ascorbic acid. Therefore, the electrolyzed water of anode side shows no dismutation activity.

(2) When an aqueous electrolytic solution containing only ascorbic acid as an electrolytic aid, at the cathode, the 2-position and 3-position hydrogen atoms of ascorbic acid are extracted by an electrophilic reaction, and ascorbic acid becomes dehydroascorbic acid. As a result, there is substantially no dismutation activity at the cathode side.

At the anode side, the ascorbic acid anion transferred from the cathode reacts with the $H^+$ generated by anode oxidation of water and returns to ascorbic acid; therefore, there is a dismutation activity. Further, the dismutation activity of the electrolyzed water of anode side is enhanced by the presence of slightly excessive $H^+$. The amount of ascorbic acid consumed by dissolved oxygen is extremely small.

In the present invention, an aqueous electrolytic solution containing only ascorbic acid as an electrolytic aid is electrolyzed; therefore, the electrolyzed water of anode side obtained has a high dismutation activity for superoxide radicals. Consequently, this electrolyzed water of anode side is useful in various applications such as sterilization, disinfection, granulation, maintenance of health or beauty, and the like. Further, since ascorbic acid is a vitamin which has been confirmed to be safe to human health, the electrolyzed water of anode side containing ascorbic acid, of the present invention has high safety.

Figure 1:
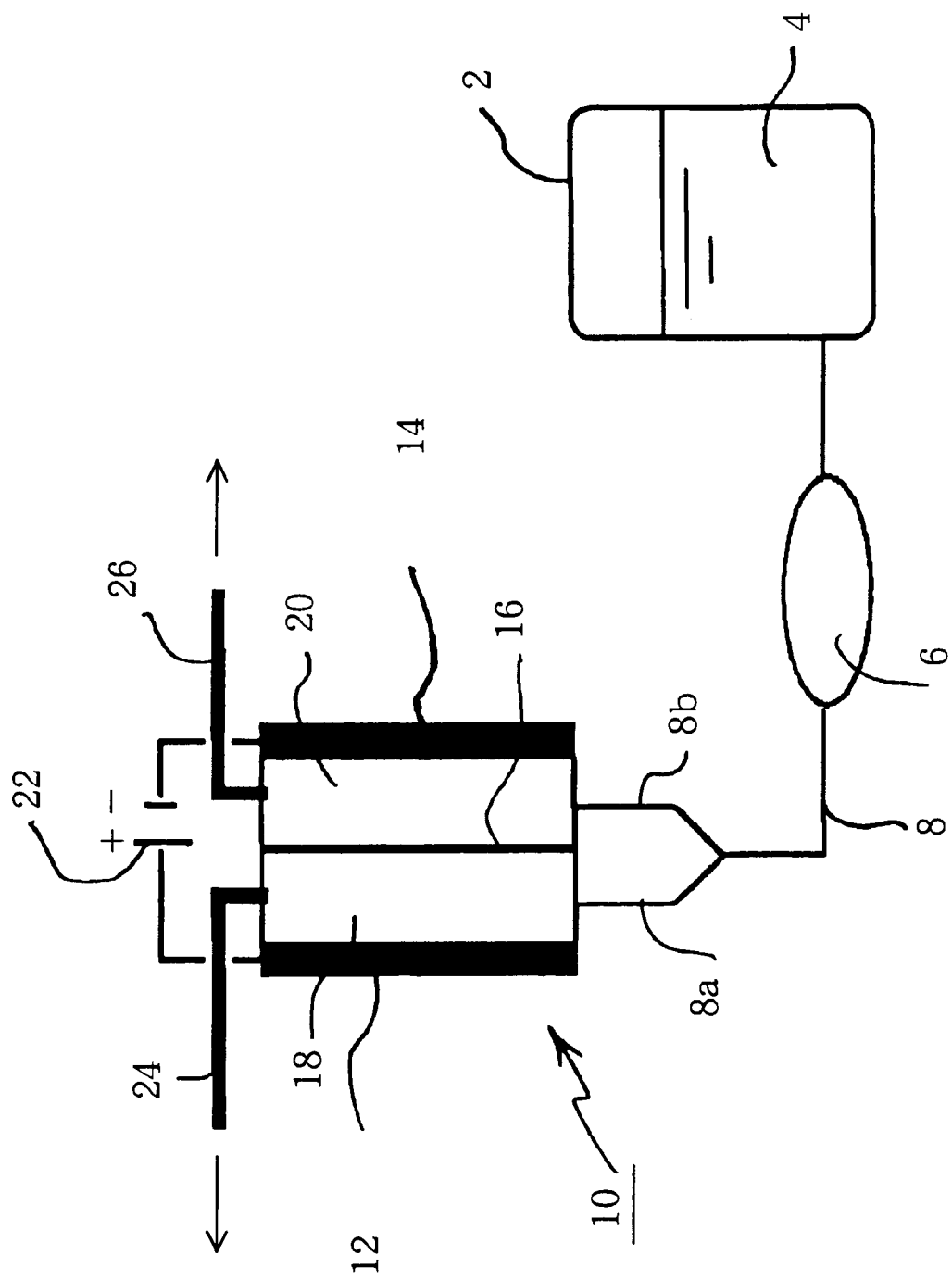
FIG. 1 is a schematic drawing showing an example of the apparatus for producing the electrolyzed water of anode side of the present invention.

2: Tank for aqueous electrolytic solution
4: Aqueous electrolytic solution
6: Pump
8: Feeding pipe for aqueous electrolytic solution
10: Electrolytic cell
12: Anode
14: Cathode
16: Separating membrane
18: Anode chamber
20: Cathode chamber
22: Electric source for electrolysis
24: Pipe for taking out electrolyzed water of anode side
26: Pipe for taking out electrolyzed water of cathode side

DETAILED DESCRIPTION OF THE PREFERRED EMBODIMENT

The present invention is described in detail below with reference to the accompanying drawings.

The electrolytic apparatus used in producing the electrolyzed water of anode side of the present invention having a dismutation activity for superoxide radicals is not critical, and any apparatus used in production of electrolyzed water can be used. That is, there can be used any electrolytic apparatus regardless of the size, the use or no use of separating membrane, etc.

FIG. 1 is a schematic drawing of an electrolytic apparatus used in production of the electrolyzed water of anode side of the present invention having a dismutation activity for superoxide radicals.

In FIG. 1, 2 is a tank for aqueous electrolytic solution and, in the tank, an aqueous electrolytic solution 4 is stored.

The aqueous electrolytic solution 4 contains 1 to 50 mM, preferably 2 to 20 mM of ascorbic acid. When the concentration of ascorbic acid is less than 1 mM, the solution has a low electric conductivity and is difficult to electrolyze. When the concentration of ascorbic acid is more than 50 mM, the electrolyzed water of anode side obtained is sticky when applied to the skin, etc. and may be inconvenient depending upon the application.

The aqueous electrolytic solution 4 desirably contains, besides ascorbic acid, substantially no electrolyte (e.g. water-soluble inorganic salt). The content of the water-soluble inorganic electrolyte is preferably 0.1 mM or less, particularly preferably 0.02 mM or less in terms of the total of individual water-soluble inorganic electrolytes.

Such an aqueous electrolytic solution 4 can be produced, for example, by dissolving ascorbic acid in purified water (pure water) such as distilled water, deionized water or the like in the above concentration.

6 is a pump placed in the middle of a feeding pipe 8 for aqueous electrolytic solution. By actuating this pump 6, the aqueous electrolytic solution 4 is sent to an electrolytic cell 10 via the feeding pipe 8.

The electrolytic cell 10 has an anode 12, a cathode 14 (the anode 12 and the cathode 14 are provided apart by a certain distance and face with each other), and a separating membrane 16 provided between the two electrodes and apart from each electrode. In the electrolytic cell 10 are formed an anode chamber 18 between the anode 12 and the separating membrane 16 and a cathode chamber 20 between the cathode 14 and the separating membrane 16. Both the anode 12 and the cathode 14 are made of an electrochemically inactive metal material. As such an electrode material, platinum, a platinum alloy or the like is preferred. The separating membrane 16 has a role of preventing the mixing of the electrolyzed water in the anode chamber 18 with the electrolyzed water in the cathode chamber 20, and is made of a material through which an electrolytic current can flow. Suitable as the separating membrane are separating membranes ordinarily used in electrolysis, such as ion exchange membrane, non-charged micro-porous membrane and the like.

The feeding pipe 8 is split into branch pipes 8a and 8b upstream of the electrolytic cell 10, and the branch pipe 8a and the branch pipe 8b are connected to the anode chamber 18 and the cathode chamber 20, respectively.

22 is an electric source for electrolysis, and its plus terminal is connected to the anode 12 and its minus terminal is connected to the cathode 14.

The aqueous electrolytic solution sent to the anode chamber 18 and the cathode chamber 20 via the branch pipe 8a and the branch pipe 8b, is electrolyzed therein. The electrolytic current density is preferably 0.003 to 0.03 A/cm$^2$, more preferably 0.01 to 0.02 A/cm$^2$. When the electrolytic current density is less than 0.003 A/cm$^2$, it is impossible to make the dissolved oxygen amount in the electrolyzed water flowing out of the anode chamber, larger than the dissolved water amount in the aqueous electrolytic solution. When the electrolytic current density is more than 0.03 A/cm$^2$, the amount of the electrolyzed water of anode side generated does not increase in proportion to an increase in electrolytic current, which is uneconomical.

Thus, by specifying the electrolytic current density in the above range, it is possible to make the dissolved oxygen amount in the electrolyzed water flowing out of the anode chamber, larger than the dissolved oxigen amount in the aqueous electrolytic solution, preferably at 8 to 15 mg/l, more preferably at 9 to 14 mg/l.

The electrolyzed water of anode side generated by the above electrolysis is taken outside via a pipe 24 for taking out the electrolyzed water of anode side. The electrolyzed water of cathode side generated by the above electrolysis is taken outside via a pipe 26 for taking out the electrolyzed water of cathode side.

The electrolytic cell 10 is provided with a separating membrane inside. An electrolytic cell with no separating membrane can also be used suitably.

Such a separating membrane-free electrolytic cell has, for example, a structure in which (1) an anode plate and a cathode plate are provided closely to each other with no separating membrane placed between the two electrode plates, (2) electrolysis can be conducted while continuously feeding an aqueous electrolytic solution into between the anode plate and the cathode plate, and (3) the electrolyzed water of anode side in the vicinity of the anode plate surface can be taken out continuously from downstream of the anode plate. As a specific example, there is an electrolytic cell disclosed in Japanese Patent Application laid open 6-246272.

The dismutation activity for superoxide radicals, possessed by an electrolyzed water can be examined by measuring the superoxide radicals signal of the electrolyzed water using an electron spin resonance (ESR) apparatus described later.

EXAMPLES

The present invention is described more specifically below by way of Examples.

Example 1

An aqueous electrolytic solution containing ascorbic acid was electrolyzed using an electrolytic apparatus shown in FIG. 1. In an electrolytic cell were arranged in parallel 5 platinum plates each of 7.5 cm×11.5 cm at 2.5 mm intervals, and a non-charged separating membrane was interposed between each two adjacent platinum plates. The platinum plates were used as an anode and a cathode alternately, whereby 4 electrolytic cells were prepared in series in one integral structure. The electrolytic cell capacity was 86.4 ml. Into the electrolytic cell was fed the aqueous electrolytic solution at a rate of 2,000 ml/min, and an electrolyzed water of anode side and an electrolyzed water of cathode side were obtained. The electrolytic current density was controlled at 0.02 A/cm$^2$.

The aqueous electrolytic solution was prepared by adding ascorbic acid to deionized water in a concentration of 2 mM. Since deionized water was used, the content of water-soluble inorganic salt in the aqueous electrolytic solution was very low (less than 0.01 mM).

The electrolyzed waters of anode side and cathode side obtained were measured for dismutation activity for superoxide radicals, using an ESR apparatus, as described below.

(1) Generation of superoxide radicals

Superoxide radicals were generated using 2 mM of hypoxanthine and 0.4 mM unit/ml of xanthine oxidase.

(2) Spin trap by DMPO

The following materials were placed in a flat cell.

2 mM hypoxanthine-phosphate buffer solution 50 μl 5.5 mM DETAPAC (diethylenetriaminepentaacetic acid)-phosphate buffer solution 35 μl DMPO (5,5-dimethyl-1-pyrroline-N-oxide) 16 μl 0.4 unit/ml xanthine oxidase-phosphate buffer solution 50 μl The flat cell was set in an ESR apparatus. After 1 minute, sweeping was started to examine the presence or absence of a signal based on superoxide radicals.

(3) ESR measurement conditions

Measurement temperature: room temperature

Microwave output: 3.7 mW

Magnetic field: 339.1 mT±5.5 mT

Magnetic field modulation: 100 kHz (outside modulation mode)

Modulation width: 0.1 mT

Response time: 0.12 sec

Sweeping time: 1 min (4) Results of measurement

Figure 2:
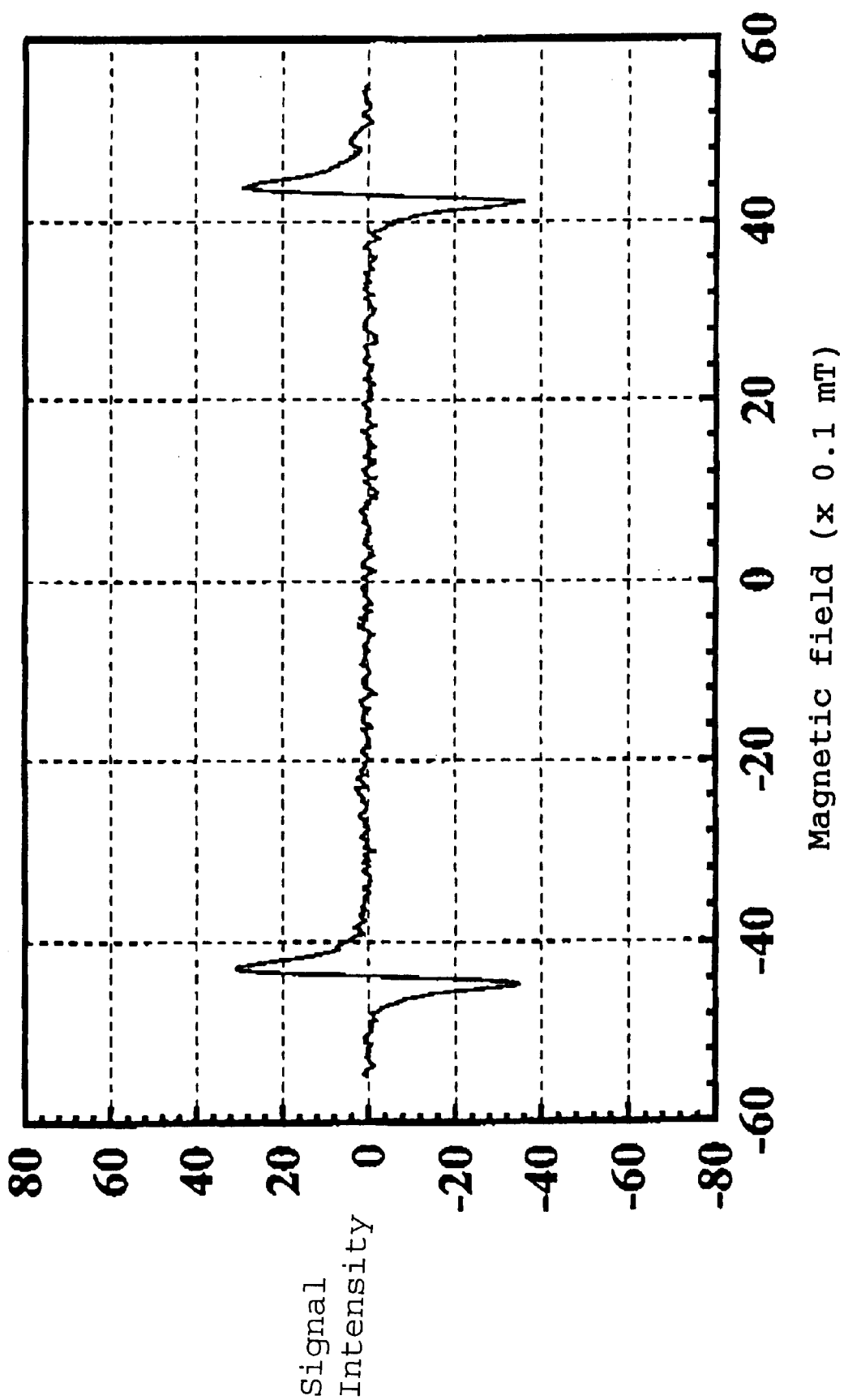
FIG. 2 is an ESR spectrum showing the dismutation ability for superoxide radicals of the electrolyzed water of anode side of Example 1.
Figure 3:
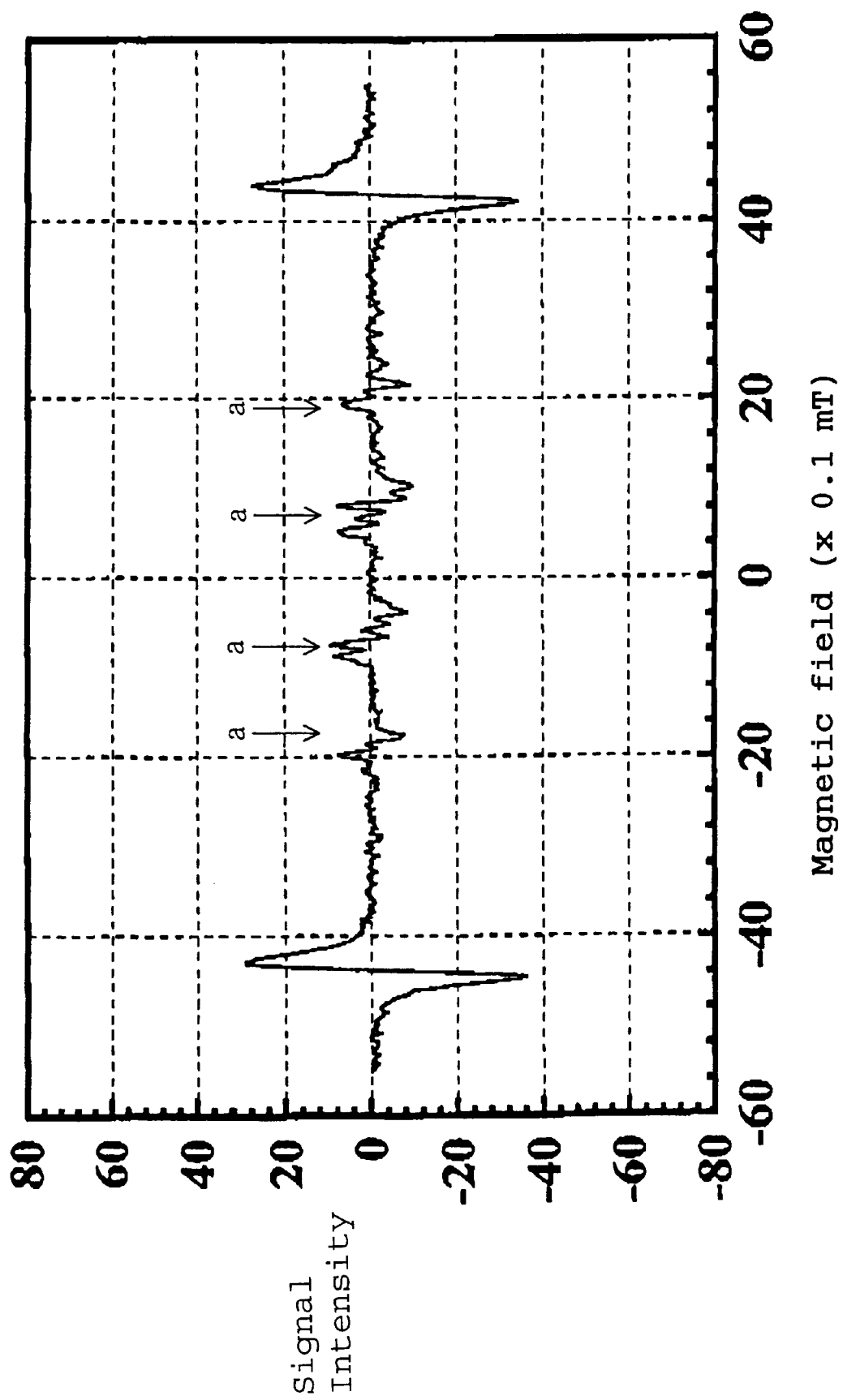
FIG. 3 is an ESR spectrum of superoxide radicals, obtained with the electrolyzed water of cathode side of Example 1.

The ESR spectra obtained are shown in FIG. 2 and FIG. 3. FIG. 2 is an ESR spectrum when the test sample was the electrolyzed water of anode side. There is no signal of superoxide radicals. Therefore, it is clear that superoxide radicals dismutated and almost disappeared.

Incidentally, the amount of dissolved oxygen was 14.99 mg/l.

FIG. 3 is an ESR spectrum when the test sample was the electrolyzed water of cathode side. There is a signal of superoxide radicals (a signal shown by arrows a in FIG. 3). Therefore, it is clear that superoxide radicals did not disappear and dismutate.

Example 2

Electrolyzed water (an electrolyzed water of anode side and an electrolyzed water of cathode side) were produced in the same manner as in Example 1 except that the ascorbic acid concentration in aqueous electrolytic solution was changed to 50 mM and the current density was changed to 0.01 A/cm$^2$.

Each of the electrolyzed water of anode side and the electrolyzed water of cathode side was measured for the signal of superoxide radicals using an ESR apparatus, in the same manner as in Example 1.

Figure 4:
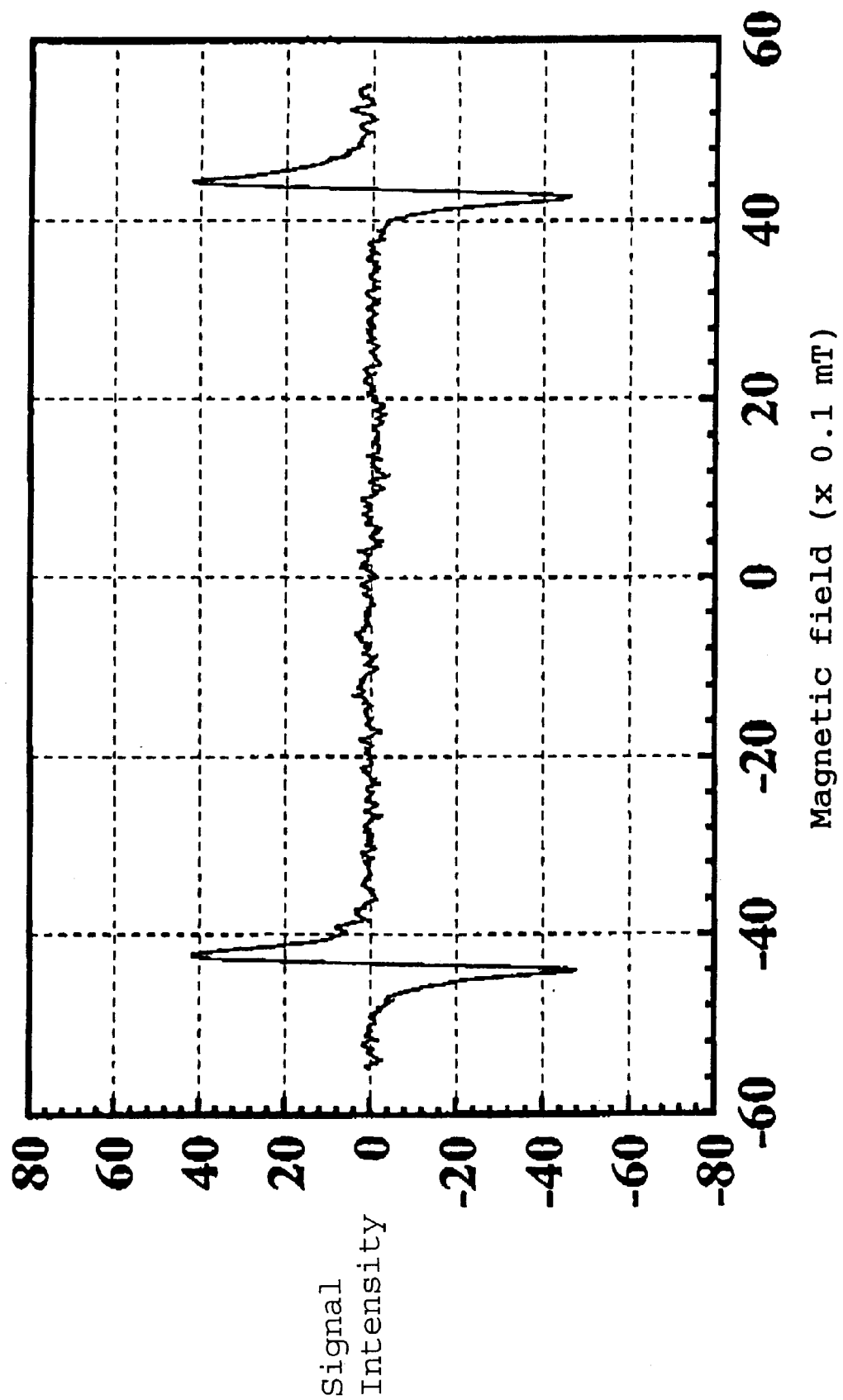
FIG. 4 is an ESR spectrum showing the dismutation ability for superoxide radicals of the electrolyzed water of anode side of Example 2.
Figure 5:
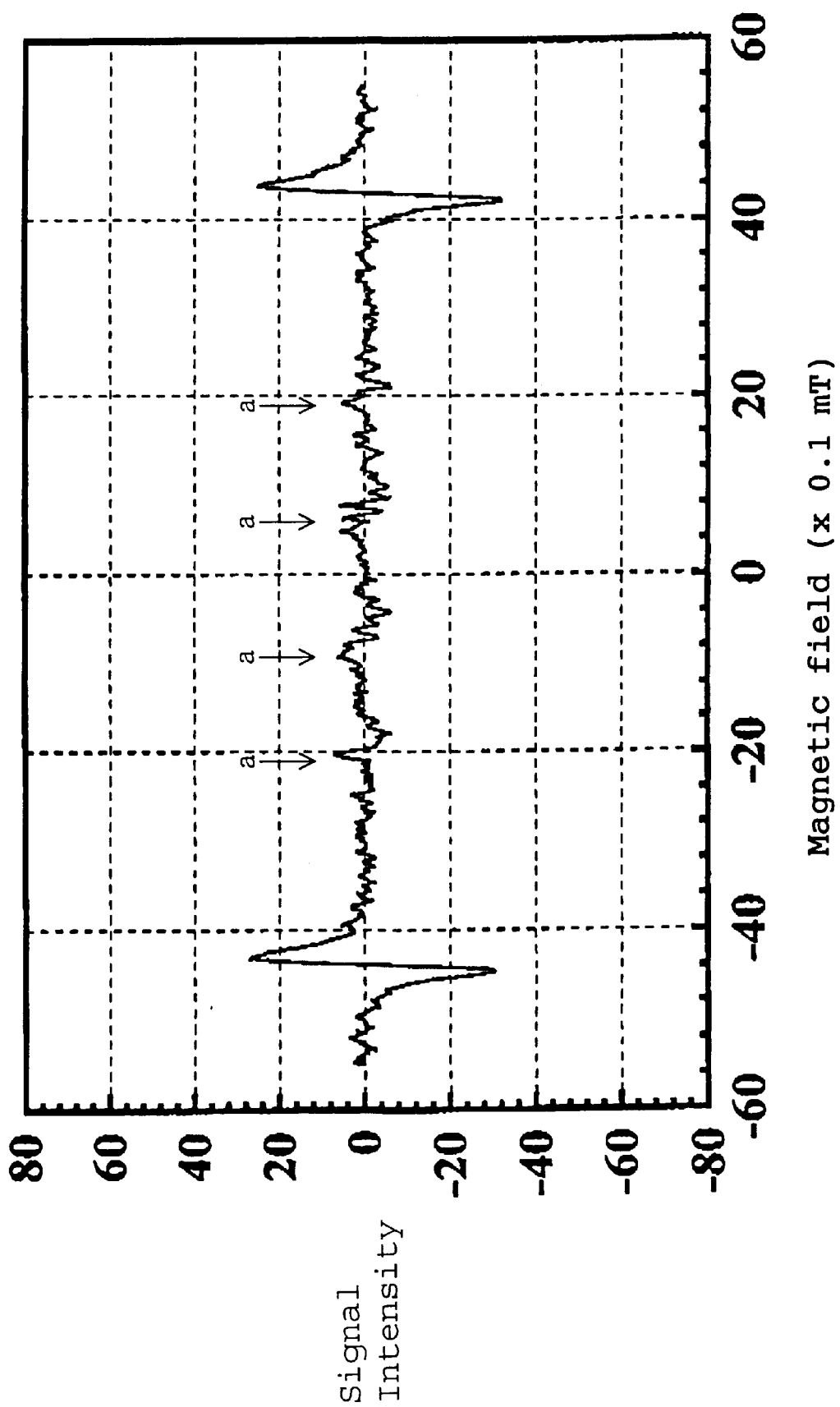
FIG. 5 is an ESR spectrum of superoxide radicals, obtained with the electrolyzed water of cathode side of Example 2.

The ESR spectra obtained are shown in FIG. 4 and FIG. 5. FIG. 4 is an ESR spectrum when the test sample was the electrolyzed water of anode side. There is no signal of superoxide radicals. Therefore, it is clear that superoxide radicals dismutated and almost disappeared.

Incidentally, the amount of dissolved oxygen was 12.3 mg/l.

FIG. 5 is an ESR spectrum when the test sample was the electrolyzed water of cathode side. There is a signal of superoxide radicals (a signal shown by arrows a in FIG. 5). Therefore, it is clear that superoxide radicals did not disappear and dismutate.

(Performance test for electrolyzed water of anode side)

The electrolyzed water of anode side obtained in Example 2 was subjected to an organoleptic test (a skin care test). For comparison, an electrolyzed water of anode side (a strongly acidic water) obtained by electrolyzing an aqueous NaCl (0.25% by mass) solution under the same conditions using the same apparatus, was subjected to the same organoleptic test.

The organoleptic test was conducted as follows.

(1) Testees: 14 healthy women who tended to have a rough skin.

(2) Test method

The electrolyzed water of anode side (the present invention) obtained by electrolyzing an aqueous electrolytic solution containing ascorbic acid was coated on the hands and faces of 7 testees of the above 14 testees twice a day for 21 days; and the electrolyzed water of anode side (comparison) obtained by electrolyzing an aqueous electrolytic solution containing NaCl was coated on the hands and faces of other 7 testees in the same frequency for the same period.

The test results are shown in Table 1.

TABLE 1

| Results of organoleptic (rough skin) test | | |
|---|---|---|
| | Testees on ascorbic acid-containing electrolyzed water of anode side | Testees on NaCl-containing electrolyzed water of anode side |
| Irritation was felt. | 0/7 (0%)[1] | 3/7 (43%) |
| Moisture retention was felt. | 6/7 (86%)[2] | 2/7 (29%) |
| There was refreshing feeling. | 7/7 (100%) | 6/7 (86%) |
| There was an odor. | 0/7 (0%) | 6/7 (86%) |
| There was a whitening effect. | 3/7 (43%) | 2/7 (29%) |
| Rough skin improved. | 6/7 (86%) | 4/7 (57%) |

[1] 0/7 (0%) means that no one (0%) of 7 (total) testees felt irritation.
[2] 6/7 (86%) means that 6 (86%) out of 7 (total) testees felt moisture retention.

The electrolyzed water of anode side obtained by electrolyzing an aqueous electrolytic solution containing NaCl is a so-called electrolyzed water used ordinarily, and has a pH of 2.5 and an oxidation-reduction potential (ORP) of 1,250 mV. The electrolyzed water of anode side of the present invention was free from irritation or odor and, moreover, was superior also in moisture retention to the electrolyzed water of anode side obtained by electrolyzing an aqueous electrolytic solution containing NaCl. The reason for such favorable properties of the electrolyzed water of anode side of the present invention is believed to be that the present electrolyzed water of anode side has an anti-oxidant action enhanced by electrolysis.

Example 3

Electrolyzed waters (an electrolyzed water of anode side and an electrolyzed water of cathode side) were produced in the same manner as in Example 1 except that the ascorbic acid concentration in aqueous electrolytic solution was changed to 20 mM and the current density was changed to 0.02 A/cm$^2$.

Each of the electrolyzed water of anode side and the electrolyzed water of cathode side was measured for the signal of superoxide radicals using an ESR apparatus, in the same manner as in Example 1.

Figure 6:
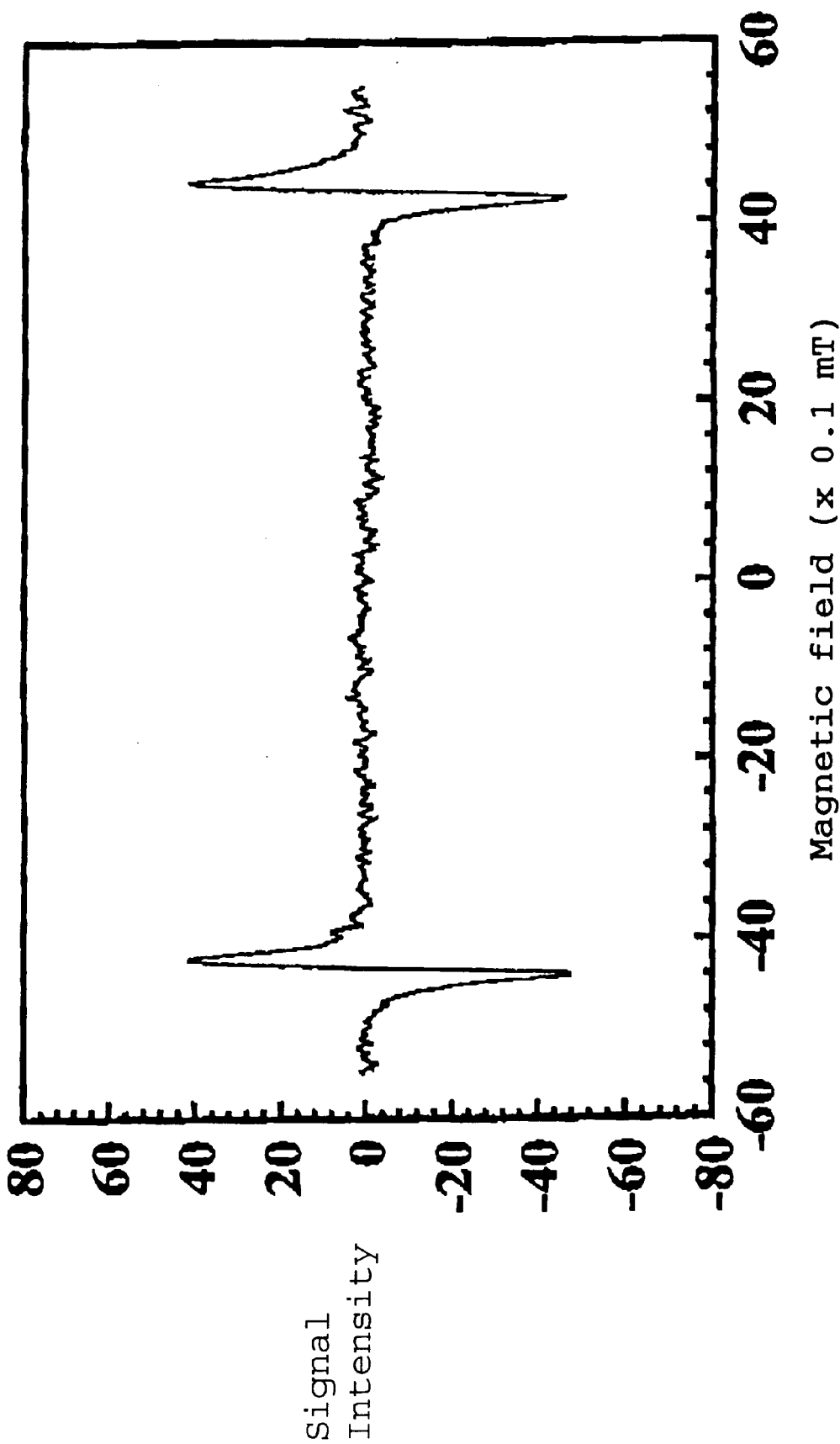
FIG. 6 is an ESR spectrum showing the dismutation ability for superoxide radicals of the electrolyzed water of anode side of Example 3.
Figure 7:
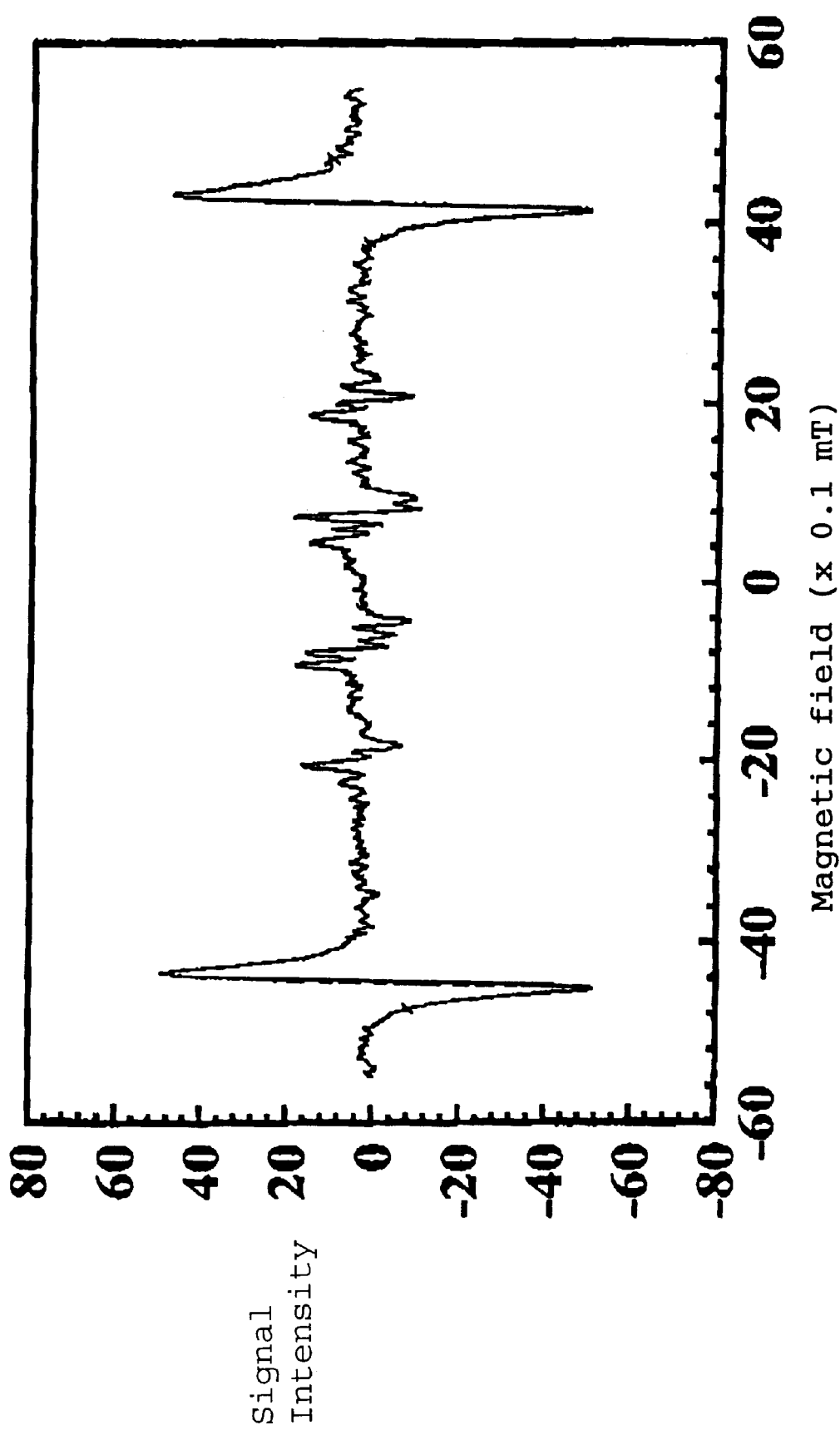
FIG. 7 is an ESR spectrum of superoxide radicals, obtained with the electrolyzed water of cathode side of Example 3.

The ESR spectra obtained are shown in FIG. 6 and FIG. 7. FIG. 6 is an ESR spectrum when the test sample was the electrolyzed water of anode side. There is no signal of superoxide radicals. Therefore, it is clear that superoxide radicals dismutated and almost disappeared.

FIG. 7 is an ESR spectrum when the test sample was the electrolyzed water of cathode side. There is a signal of superoxide radicals (a signal shown by arrows a in FIG. 7). Therefore, it is clear that superoxide radicals did not disappear and dismutate.

Comparative Example 1

Electrolysis was conducted in the same manner as in Example 1 except that 2 mM NaCl was used as an aqueous electrolytic solution. Each of the electrolyzed water of anode side and the electrolyzed water of cathode side, both obtained by the electrolysis was measured for ESR spectra in the same manner as in Example 1.

Figure 8:
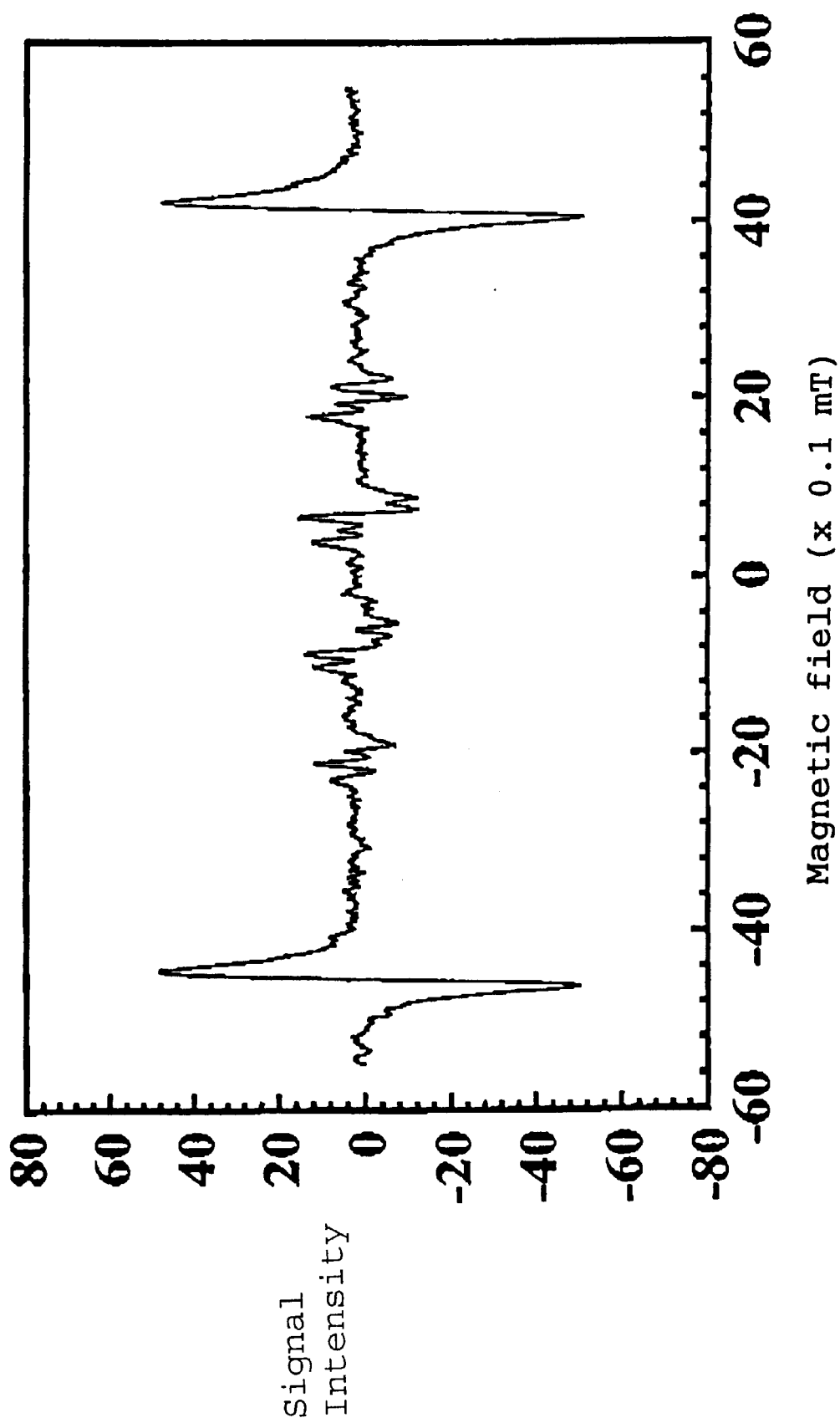
FIG. 8 is an ESR spectrum of superoxide radicals, obtained with the electrolyzed water of anode side of Comparative Example 1.
Figure 9:
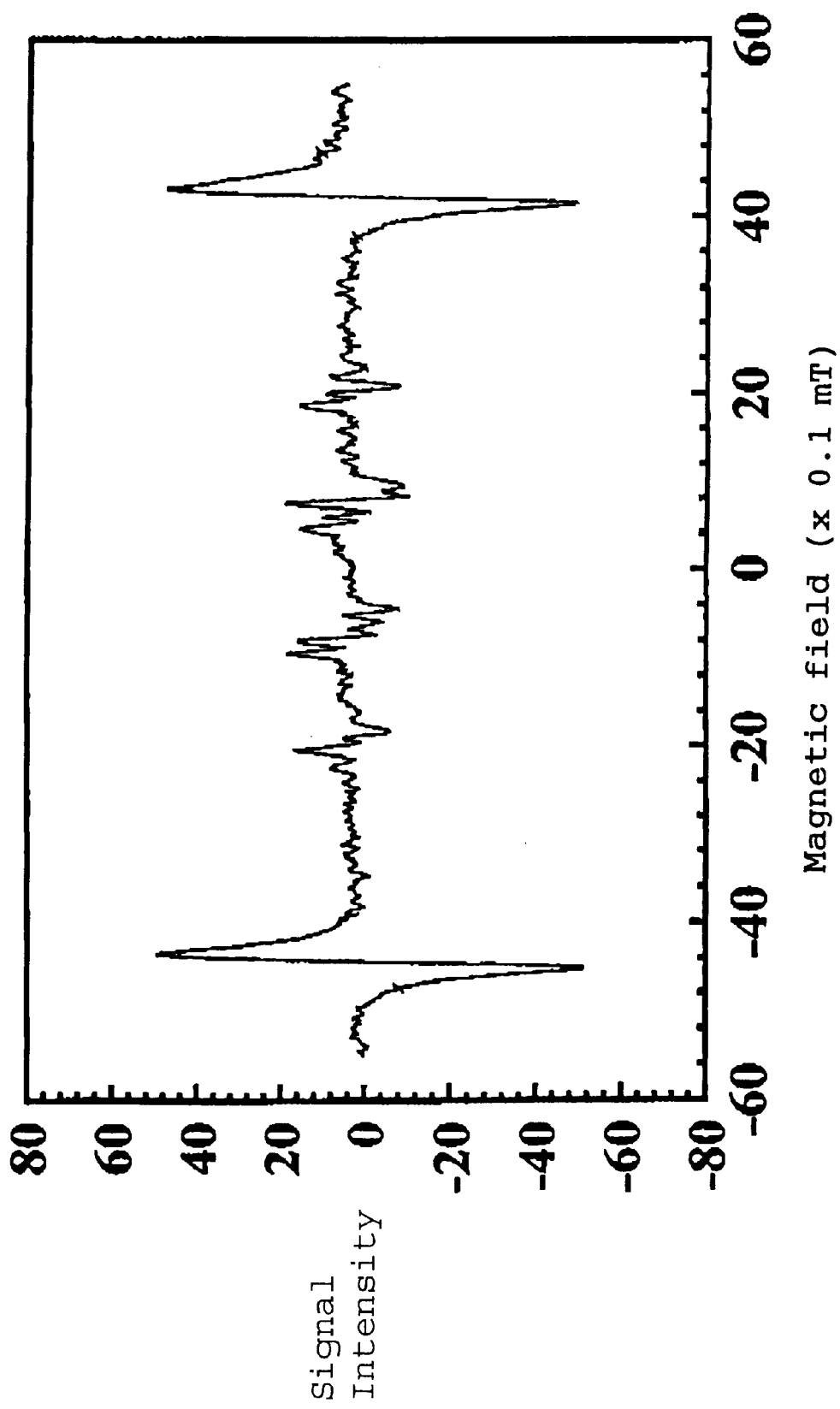
FIG. 9 is an ESR spectrum of superoxide radicals, obtained with the electrolyzed water of cathode side of Comparative Example 1.

The ESR spectra of the electrolyzed water of anode side and the electrolyzed water of cathode side are shown in FIG. 8 and FIG. 9, respectively. A signal of superoxide radicals is seen in each of the electrolyzed waters, and it is clear that any of the two electrolyzed waters had no dismutation activity for superoxide radicals.

Comparative Example 2

Figure 10:
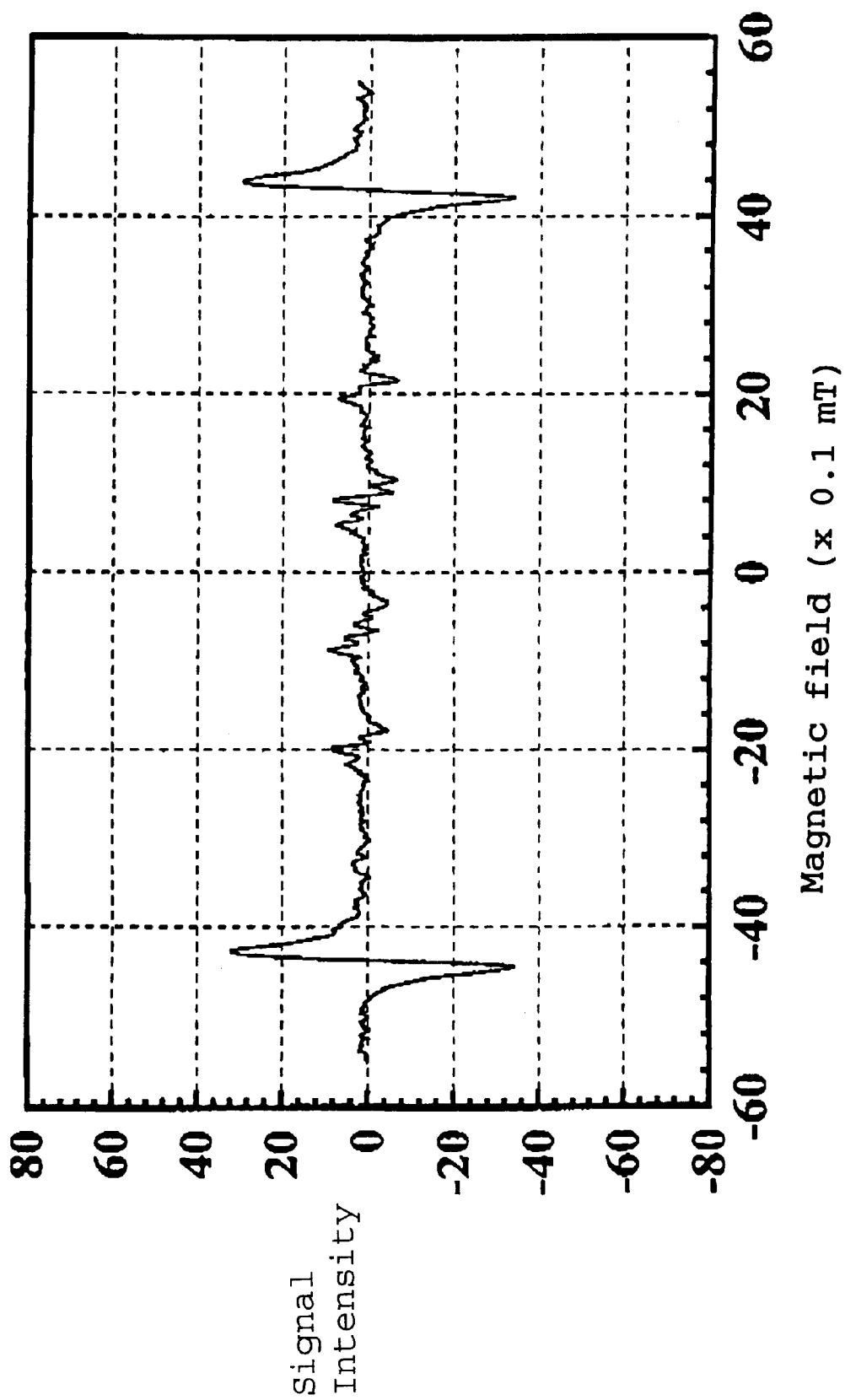
FIG. 10 is an ESR spectrum of superoxide radicals, obtained with distilled water per se of Comparative Example 2.

Distilled water was not electrolyzed and was per se measured for dismutation activity for superoxide radicals in the same manner as in Example 1. The ESR spectrum obtained is shown in FIG. 10. In the case of this pure water, there is no disappearance of superoxide radicals and accordingly there was no dismutation activity.

Incidentally, the amount of dissolved oxygen was 9.65 mg/l.

Reference Example 1

When ascorbic acid is dissolved in purified water, the dissolved oxygen in purified water is consumed by ascorbic acid and its amount becomes ordinarily 8 mg/l or less. In contrast, when an aqueous ascorbic acid solution is electrolyzed, oxygen is generated by the electrolysis of water at anode. Therefore, in electrolysis of an aqueous ascorbic acid solution, the oxygen generated by electrolysis is added to the dissolved oxygen already present in the solution before electrolysis, whereby the electrolyzed water of anode side contains a larger amount of dissolved oxygen than the solution before electrolysis does.

Therefore, the aqueous ascorbic acid solution before electrolysis and the electrolyzed water can be easily distinguished by comparing the dissolved oxygen amounts therein, unless an extremely long time has passed since electrolysis.

Figure 11:
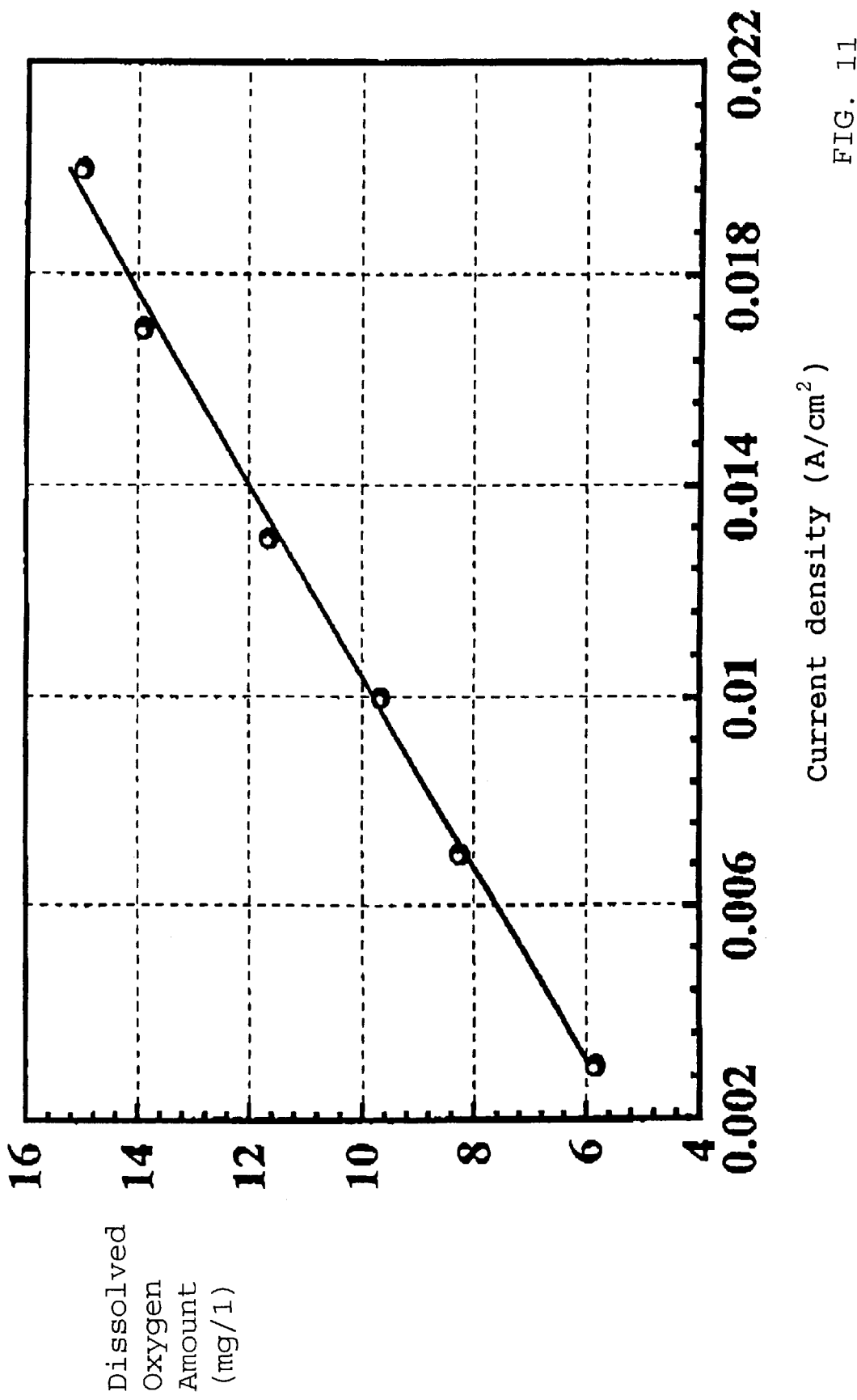
FIG. 11 is a graph showing a relation between electrolytic current density and dissolved oxygen amount when an aqueous electrolytic solution was electrolyzed in Example 1.

FIG. 11 is a graph showing a relation between electrolytic current density and dissolved oxygen amount when the aqueous ascorbic acid solution of Example 1 was electrolyzed using the same electrolytic apparatus as in Example 1. As seen in FIG. 11, electrolysis inevitably gives an increased dissolved oxygen amount in the electrolyzed water of anode side.

Incidentally, the above dissolved oxygen is the same as generated in electrolysis using NaCl as an electrolytic aid, and has an action contributing to skin regeneration or skin restoration.

What is claimed is:

1. An electrolyzed water of anode side containing less than 0.1 mM of a water-soluble inorganic salt, 1 to 50 mM of ascorbic acid and 8 to 15 mg/l of dissolved oxygen and having a dismutation activity for superoxide radicals.

2. A process for producing an electrolyzed water of anode side having a dismutation activity for superoxide radicals, which comprises electrolyzing an aqueous electrolytic solution containing less than 0.1 mM of a water-soluble inorganic salt and 1 to 50 mM of ascorbic acid and then taking out the electrolyzed water of anode side generated.

3. A process for producing an electrolyzed water of anode side having a dismutation activity for superoxide radicals, according to claim 2, wherein the electrolysis is conducted using an electrolytic cell having a separating membrane.

4. A process for producing an electrolyzed water of anode side having a dismutation activity for superoxide radicals, according to claim 2, wherein the electrolysis is conducted at a current density of 0.003 to 0.03 A/cm$^2$.

5. A process for producing an electrolyzed water of anode side having a dismutation activity for superoxide radicals, according to claim 2, wherein an aqueous electrolytic solution containing less than 0.1 mM of a water-soluble inorganic salt and 1 to 50 mM of ascorbic acid is fed into a continuous flowing type electrolytic cell having a separating membrane, at a flow rate of 500 to 3,000 ml/min and is electrolyzed continuously at a current density of 0.003 to 0.03 A/cm$^2$.

* * * * *